United States Patent [19]

Behme et al.

[11] Patent Number: 4,625,608

[45] Date of Patent: Dec. 2, 1986

[54] MICROTOMES

[75] Inventors: Werner Behme, Walldorf; Manfred Berleth, Eppelheim, both of Fed. Rep. of Germany

[73] Assignee: Parke, Davis & Company, Morris Plains, N.J.

[21] Appl. No.: 696,363

[22] Filed: Jan. 30, 1985

[30] Foreign Application Priority Data

Feb. 7, 1984 [DE] Fed. Rep. of Germany ....... 3404097

[51] Int. Cl.$^4$ ............................................. G01N 1/06
[52] U.S. Cl. ....................................... 83/713; 83/412; 83/915.5
[58] Field of Search ................. 83/713, 412, 414, 714, 83/703, 915.5

[56] References Cited

U.S. PATENT DOCUMENTS

| | | | |
|---|---|---|---|
| 2,482,853 | 9/1949 | Ladd | 83/915.5 X |
| 3,077,806 | 2/1963 | Hellstrom | 83/412 X |
| 3,603,189 | 9/1971 | Stachl | 83/412 |
| 4,377,958 | 3/1983 | Leighton | 83/412 X |

Primary Examiner—Donald R. Schran
Attorney, Agent, or Firm—Alan H. Spencer

[57] ABSTRACT

A microtome has a specimen holder which executes a vertical up and down movement relative to a cutting knife and which has a guide mechanism in which a sleeve is arranged so as to be horizontally displaceable. The sleeve is provided at its front end with a specimen clamping mechanism and in its interior with a micrometer nut which is secured against axial displacement and through which extends a micrometer spindle mounted on the guide mechanism. The micrometer nut has on its outer face a toothed ring which is connected operatively to a pinion connected to an electric motor. When the electric motor is activated the sleeve is displaced in the guide mechanism. The micrometer spindle extends, on the side opposite the specimen clamping mechanism, through the guide mechanism as a stub end on which is located a mechanical cutting-thickness advance mechanism. This advances the sleeve together with the specimen clamping mechanism, by a cutting-thickness set from outside the microtome, always in an uppermost position of the specimen holder.

6 Claims, 6 Drawing Figures

MICROTOMES

BACKGROUND OF THE INVENTION

This invention is concerned with improvements relating to microtomes.

In known microtomes a specimen holder may be provided having a specimen clamping mechanism for clamping a specimen to be cut. The specimen clamping mechanism is moved vertically up and down relative to a cutting knife which cuts the specimen during the downward movement of the specimen clamping mechanism. The specimen clamping mechanism is movable between an uppermost position in which it is above the cutting knife, and a lowermost position in which it is below the cutting knife.

In addition to this vertical movement the specimen clamping mechanism is also movable horizontally towards and away from the cutting knife between a rearmost position and a forwardmost position. In the rearmost position the specimen clamping mechanism is at its furthest horizontal distance from the cutting knife, and in the forwardmost position the specimen clamping mechanism is at its closest horizontal distance to the cutting knife.

In known rotary microtomes a mechanical drive is provided for executing a rough feed movement of the specimen clamping mechanism along the horizontal towards the cutting knife, and for executing a rough return movement of the specimen clamping mechanism along the horizontal away from the cutting knife. The mechanical drive may also be able to provide a rough cutting thickness adjustment of the specimen clamping mechanism towards the cutting knife along the horizontal after each cut has been made.

This kind of mechanical drive may include a movable shaft connected to a hand wheel located outside the microtome. In order to actuate the rough feed the hand wheel must be manually actuated. However, this manual actuation involves a high outlay and is inconvenient to operate.

SUMMARY OF INVENTION

An object of the present invention is to provide an improved microtome which overcomes the aforementioned disadvantages.

According to the present invention there is provided a microtome comprising a cutting knife, a specimen holder adapted to be displaced in a first direction relative to the cutting knife, said specimen holder including guide means and a sleeve, specimen clamping means arranged at one end of the sleeve, the sleeve being adapted to be displaced relative to the guide means in a direction substantially transverse to the first direction, and a drive motor for displacing the sleeve relative to the guide means.

Typically the first direction would, in use, be substantially parallel to the vertical.

Preferably the guide means includes a micrometer nut disposed within the sleeve, and secured against axial movement relative thereto, and a micrometer spindle is mounted on the guide means and extends through the micrometer nut in threaded engagement therewith.

Desirably a toothed ring is provided on an outer surface of the micrometer nut, and a pinion is connected to the drive motor, the toothed ring being operatively connected to the pinion.

Advantageously the motor is an electric motor. By means of the motor it is possible to rotate the micrometer nut relative to the micrometer spindle, by way of the pinion and the toothed ring, and consequently to displace the sleeve, to which the specimen clamping means is fastened, horizontally in relation to the micrometer spindle. This horizontal displacement of the specimen clamping means can advantageously be carried out at different speeds continuously or in steps with different step lengths, so that it is possible in a very simple way to bring the specimen clamping means, and consequently a specimen to be cut, up to the cutting knife rapidly and to start cutting the specimen clamped in the specimen clamping means in rough steps until a precisely defined cutting surface is obtained, after which appropriate thin-section cuts can be made.

The electric motor may be secured to the guide means, and the pinion can be arranged axis-parallel to the micrometer spindle and can have a length which corresponds at least to the maximum horizontal movement of the specimen clamping means. In this way, the electric motor can accurately follow the vertical movement of the guide means and consequently the vertical movement of the micrometer spindle and micrometer nut. Thus, the pinion connected to the electric motor is always operatively connected to the micrometer nut, and the specimen clamping means can be displaced horizontally by the motor at any time and in any position of the specimen holder. The specimen clamping means can advantageously be displaced horizontally in the two opposite directions, so that, as a result, not only is it possible to execute a rough feed of the specimen clamping mechanism up to a first-cut position of the specimen and to make rough cutting-thickness adjustments in order to make rough first cuts of the specimen, but it is also simply possible to move back the specimen clamping means away from the cutting knife in any position of the specimen holder.

It has been found advantageous to provide a gearwheel, which is rotatable on a mounting secured to the sleeve, at a position intermeditae between the pinion and the toothed ring of the micrometer nut. The intermediate gearwheel may have a width equal to the width of the toothed ring of the micrometer nut. By means of this gearwheel a reliable operative connection is provided between the pinion and the micrometer nut. Advantageously, it is sufficient to provide in the sleeve of the specimen holder a small recess, through which the intermediate gearwheel partially extends, in order to make the operative connection between the pinion and the toothed ring of the micrometer nut. The recess may be dimensioned so that it is just large enough to receive the gearwheel, in order to protect the interior of the specimen holder against dust and dirt.

In one embodiment of the invention, the micrometer spindle extends through the guide means to a stub end remove from the specimen clamping means, on which end is located a mechanical cutting-thickness advancement mechanism. When the specimen holder is in an uppermost position, above the cutting knife, the advancement mechanism advances the sleeve together with the specimen clamping means by a cutting-thickness adjustment which is set from outside the microtome in order to make a thin-section cut. It is possible by means of this mechanical cutting-thickness advancement mechanism to advance the cutting-thickness automatically and accurately after each thin-section cut, and only the micrometer spindle rotates in the micrometer nut, which does not rotate, during this cutting-thickness advance. It is possible, even during this mechanical cutting-thickness advance, to maintain the operative connection between the pinion connected to the electric motor and the toothed ring of the micrometer nut at any time and in any position of the specimen clamping means. It is thereby also possible to combine advantageously this mechanical cutting-thickness advance with the rough cutting-thickness advance carried out by means of the electric motor, and thus to obtain maximum cutting thicknesses for the first cut.

The horizontal movement of the sleeve can be limited by limit switches between a rearmost and a forwardmost position. By means of these limit switches, the horizontal movement of the sleeve and consequently of the specimen clamping means is limited both forwards and rearwards, so that possible damage to the microtome arising from careless operation is prevented. A press-button control triggering the feed movement towards the cutting knife along the horizontal can indicate visually by flashing when the forwardmost position is reached, as a result of the constant automatic advance of the specimen clamping means by means of the cutting-thickness advance mechanism or as a result of the feed driven by the electric motor; the electric motor for the rough feed of the specimen clamping means may be actuated by means of this press-button control. Likewise, a press-button control triggering the return movement away from the cutting knife along the horizontal can indicate visually by flashing when the rearmost position of the specimen clamping means is reached, as a result of the return movement driven by the electric motor; the electric motor may be actuated in the opposite direction of rotation by means of this press-button control to execute the return movement of the specimen clamping means.

The guide means may interact, during vertical movement, with a limit switch connected to a cut counter and/or to an electronic device by means of which the drive motor can be triggered. It is therefore possible, by means of this limit switch, both to count the cuts made and to control the motor-driven rough cutting-thickness advance of the specimen clamping mechanism. In one embodiment of the invention the rough cutting-thickness advance is carried out at a lowermost position of the specimen clamping means, below the cutting knife, after the guide means has executed a downward vertical movement. However, this at the same time necessitates a retraction of the specimen clamping means away from the cutting knife over a distance greater than the sum of the maximum possible rough cutting-thickness advance and the precise cutting-thickness advance set by the mechanical cutting-thickness advancement mechanism. In this way, during the vertical upwards movement of the specimen clamping means to the uppermost position, the cutting knife at no time touches a specimen to be cut, so that the knife edge of the cutting knife is protected and the cut surface of the specimen is not scratched by the cutting knife as it moves back.

The limit switches limiting the horizontal movement of the sleeve can be connected to the electronic device.

These limit switches may be microswitches known per se. The electronic device ensures that after reaching one end position the specimen clamping means can be moved only in the opposite direction. The electronic device locks switching devices coupled to these microswitches in such a way that, for example, the switching device intended for the feed movement of the specimen clamping means is blocked when the specimen clamping means is in its forwardmost position, and the switching device intended for the return movement of the specimen clamping means is blocked when the specimen clamping means is in its rearmost position.

The electric motor can be connected by conductor leads to the electronic device, by means of which it is possible to generate at least one constant voltage or a plurality of pulses of different voltage levels and/or different pulse lengths. The electric motor can be activated selectively by control means which can be actuated from outside the microtome, such that the specimen clamping means can be moved horizontally continuously or in steps, depending on the voltage value and/or the pulse length of the supply voltage to the electric motor. The control means may include a rotary switch having switch positions for setting the different pulse lengths and having an additional switch position for setting the constant voltage. The control means may include further controls for setting the different voltage levels.

Advantageously, the electric motor can execute not only continuous movements dependent on the particular voltage level, but also recurring adjusting movements exactly dependent on the particular pulse length. In this way it is possible, not only to carry out rough feed of the specimen clamping means towards the cutting knife at different speeds with great ease, but also to carry out rough cutting-thickness advancements of the specimen clamping means towards the cutting knife with the same ease, in order to make rough first cuts on a specimen until a specific thin-section cutting surface is obtained, after which the appropriate thin-section cuts are then made.

In one embodiment of the invention, the electronic device can generate two voltage levels for two different horizontal movement speeds, of which one movement speed is ten times as fast as the second movement speed. The same electronic device can generate pulses with first, second and third lengths, the second pulse length being twice as long as the first pulse length, and the third pulse length being three times as long as the first pulse length. The two voltage levels can be preselected by a press-button control switch, forming part of the control means, which can be actuated from outside the microtome. The three pulse lengths can be preselected, for example, by means of the rotary switch, forming part of the control means, which can be actuated from outside the microtome and which also has, in addition to three positions for setting the pulse length, a fourth position which activates the constant voltage. This means that continuous rough feed of the specimen clamping means is possible only when the rotary switch is in the fourth position, or that step-by-step rough cutting-thickness advance for the first cutting of a specimen is possible only when one of the three first mentioned positions of the rotary switch is preselected.

For example, specimens embedded in plastics may receive rough first cuts in cutting-thicknesses of 5 $\mu$m, 10 $\mu$m or 15 $\mu$m, whilst specimens embedded in paraffin may receive rough first cuts in cutting-thicknesses of 50 $\mu$m, 100 $\mu$m or 150 $\mu$m.

It is very convenient to operate the rough feed movement of the specimen clamping means and rough cutting-thickness advance for the first cutting of a specimen, and it is also very convenient to operate the continuous and rapid return movement of the specimen clamping means after the desired thin-section cuts of the specimen have been made. Likewise it is possible to combine the mechanical cutting-thickness advance mechanism known per se, in the form of a micrometer mechanism which can be set, for example, between 0 μm and 60 μm, with an electrical rough feed device and rough cutting-thickness advancement facility.

BRIEF DESCRIPTION OF THE DRAWINGS

Further details, features and advantages will appear from the following description of an exemplary embodiment of the invention illustated in the accompanying drawings, in which.

DETAILED DESCRIPTION

Figure 2:
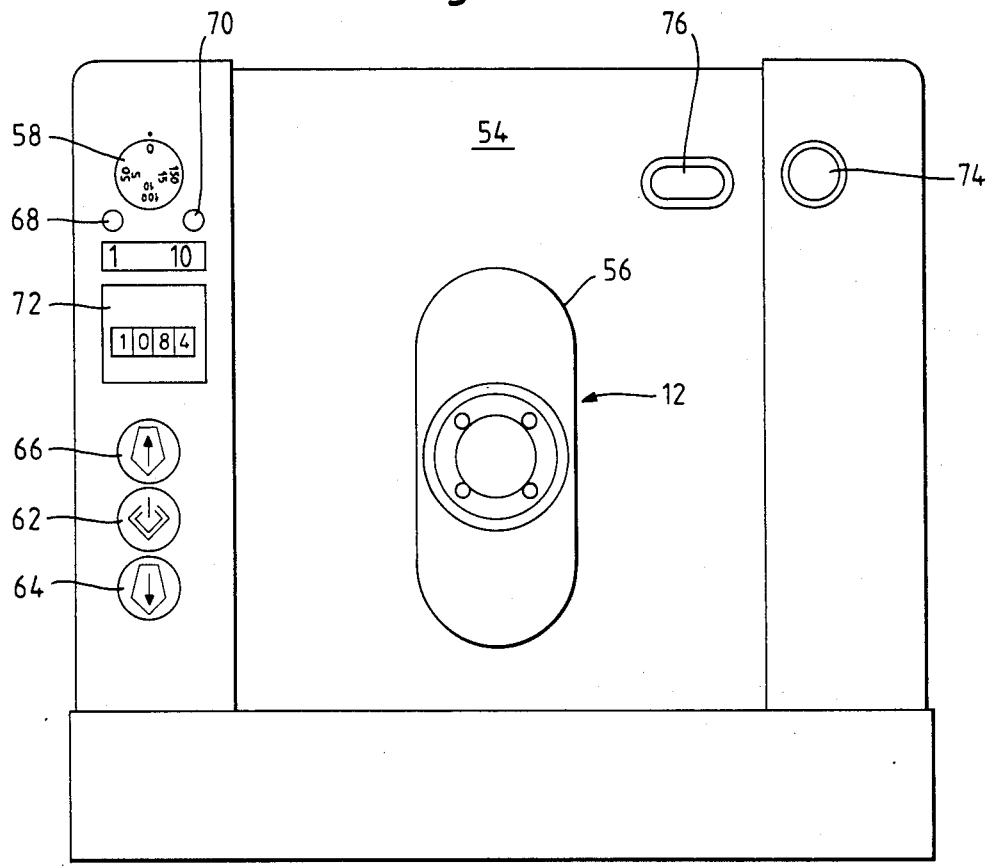
FIG. 2 shows a front view of a microtome of this type.

In the drawings a microtome 90 includes a housing 100 mounted on a base 130. A specimen holder 2 is vertically displaceable in a direction indicated by arrows A in a stand 4 relative to a cutting knife 110. The cutting knife 110 is secured to a knife holder 120 which is mounted on the base 130. In FIG. 2 the cutting knife 110 is not shown for increased clarity.

The specimen holder 2 includes guide means in the form of a guide mechanism 6 which comprises a hollow cylinder. A sleeve 8 is arranged in the guide mechanism 6 and is horizontally displaceable relative thereto along an axis 10.

Specimen clamping means in the form of a specimen clamping mechanism 12 is secured to an end face of the sleeve 8. A specimen 18 to be cut is clamped between jaws 14 and 16 of the specimen clamping mechanism 12.

A micrometer nut 20 is disposed in the interior of the sleeve 8 and is secured against axial movement relative thereto. The micrometer nut 20 is rotatably mounted to the sleeve 8 by means of ball bearings 22. A micrometer spindle 24 extends through the micrometer nut 20, and is mounted rotatably in a cover 26 of the guide mechanism 6 and is secured against axial displacement.

An outer face of the micrometer nut 20 is provided with toothed ring 28 which is operatively connected to a pinion 34 by an intermediate gearwheel 30. The pinion 34 is connected to a drive shaft 44 of an electric motor 32. The electric motor 32 is secured to the guide mechanism 6, and the pinion 34 is arranged between two bearing devices 36 and 38, so that it is axis parallel to the micrometer spindle 24. The pinion 34 has a length at least as great as the maximum horizontal movement of the specimen clamping mechanism 12 which may, for example, be of the order of about 25 mm.

Intermediate gearwheel 30, the width of which is equal to the width of the toothed ring 28, is carried rotatably on a mounting 40, secured to the sleeve 8. The intermediate gearwheel 30 extends through a slot 42 of the sleeve 8. The slot 42 is just large enough to receive the intermediate gearwheel 30 so that the interior of the sleeve 8 is substantially protected against the entry of dust and dirt. The tooth spacings of the intermediate gearwheel 30 are equal to the tooth spacings of the toothed wheel 28.

A mechanical cutting-thickness advancement mechanism, known per se, is located on a stub end 52 of the micrometer spindle 24. A lever (not shown) is pivotally mounted to the mechanism 50 so that the lever can pivot from an initial position about the axis 10, so that the pivotal movement of the lever about the axis 10 in one direction of rotation causes the mechanism 50 and the spindle 24 also to rotate about the axis 10. The lever is biassed so that following this pivotal movement it rotates in the opposite direction of rotation back to the initial position. This return movement of the lever takes place without rotation of the mechanism 50 or the spindle 24.

The specimen clamping mechanism 12 projects through an elongate slot 56 in a front plate 54 of the microtome 90.

Figure 3:
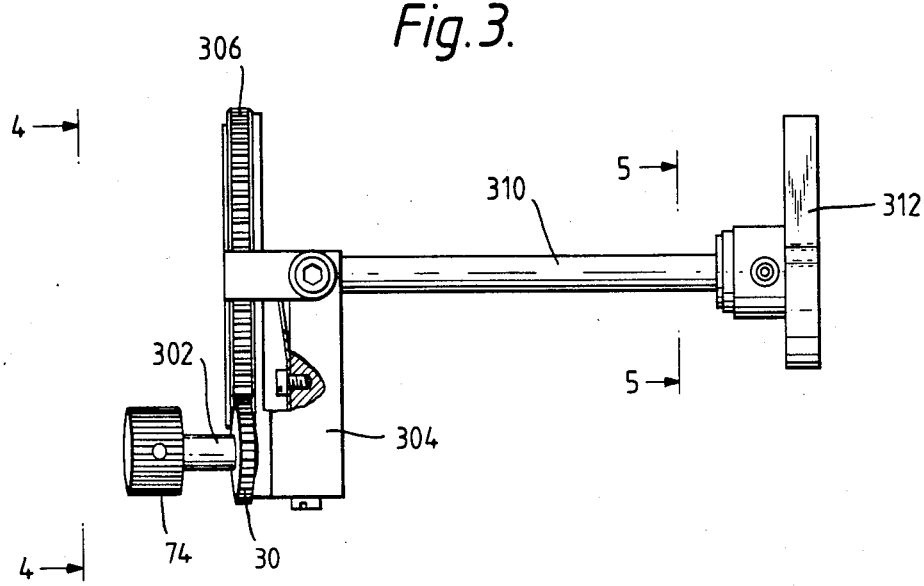
FIG. 3 is an elevation of means for adjusting the cutting-thickness advancements of a mechanical cutting-thickness advancement mechanism in a microtome according to the invention.
Figure 4:
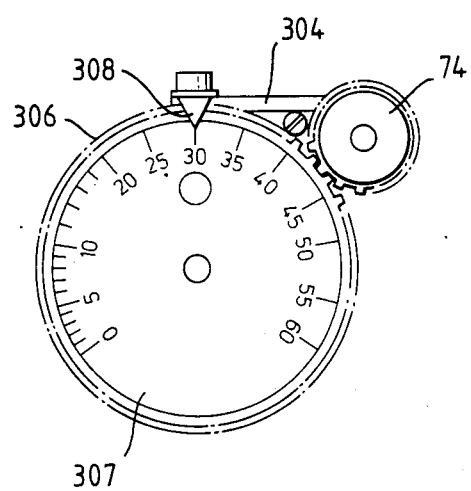
FIG. 4 is a view on lines 4—4 of FIG. 3.

The arrangement of the setting knob 74 is shown more clearly in FIGS. 3 and 4.

The setting knob 74 is connected to a toothed wheel 300 by a shaft 302. The toothed wheel 300 is rotatably mounted on a mounting 304 which can be secured to the microtome housing 100. Rotation of the setting knob 74 causes rotation of the toothed wheel 300.

The toothed wheel 300 engages a toothed wheel 306 which extends around the periphery of a setting dial 307. A front face of the setting dial 307 indicates various cutting-thicknesses which may be set, and in FIG. 5 the cutting-thickness may be set between 0 and 60 μm.

A pointer 308 is mounted to the mounting 304 and indicates the cutting-thickness which has been set on the setting dial 307. The part of the setting dial 307 in the region of the pointer 308 is visible through the inspection window 76.

Figure 5:
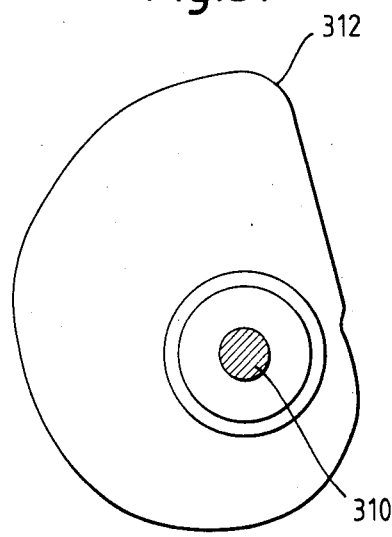
FIG. 5 is a view on lines 5—5 of FIG. 4.

The setting dial 307 is mounted on one end of a shaft 310, and on the other end of the shaft 310 a cam device 312 is disposed (see also FIG. 5). The cam device 312 can engage the lever on the mechanism 50 in a way which will be described below.

Switching devices in the form of a rotary switch 58, and three press-button controls 62, 64 and 66 are provided on the left-hand side of the front plate 54. Light emitting diodes 68 and 70, and a resettable cut counter 72 are also provided on the left-hand side of the front plate 54. A setting knob 74 is provided on the front plate 54 for setting a desired cutting-thickness indicated in an inspection window 76.

The electric motor is connected to an electronic device 84 by leads 48. The electronic device 84 is connected also to switches 58, 62, 64 and 66, and to light emitting diodes 68 and 70.

Figure 1:
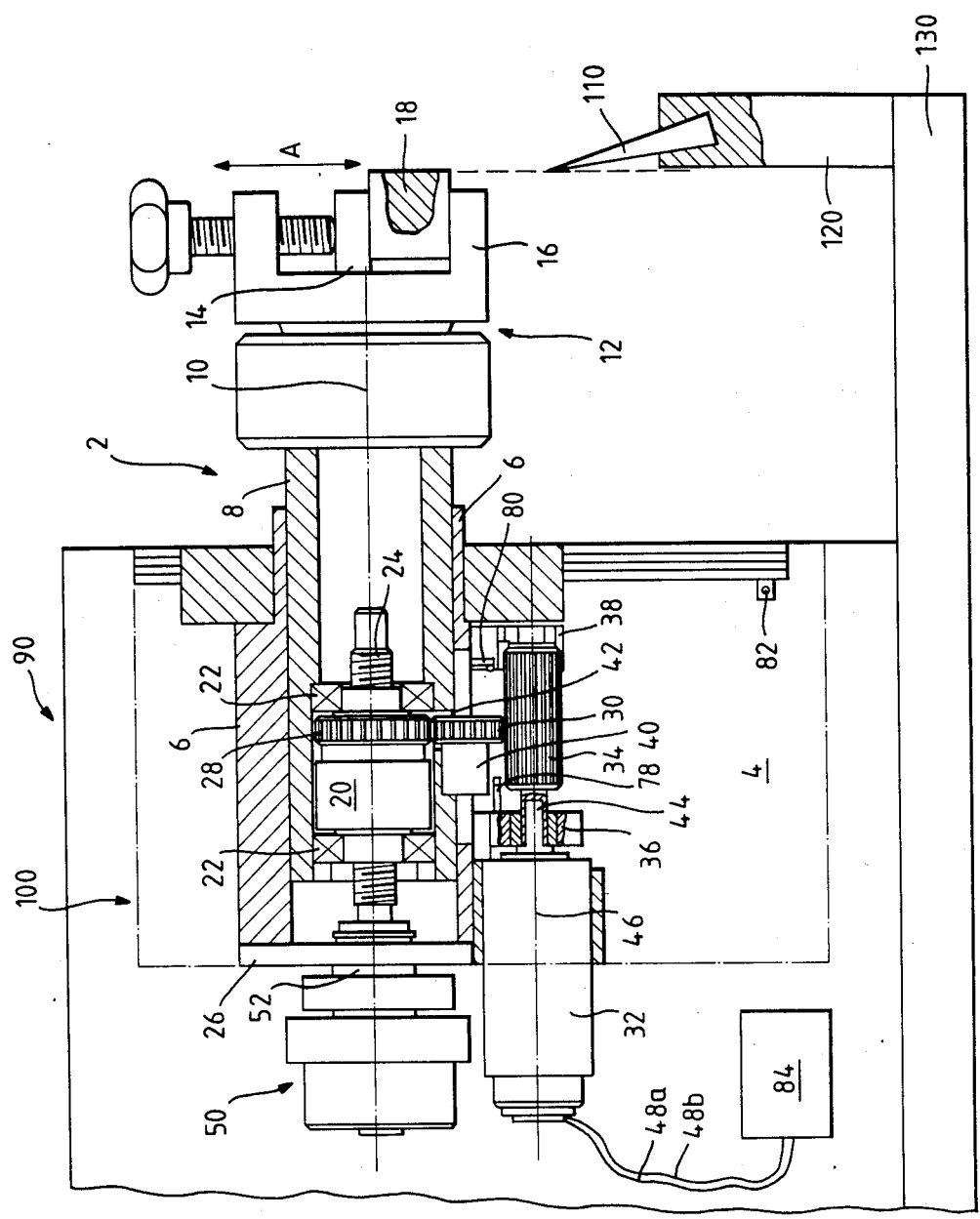
FIG. 1 shows a longitudinal section through a specimen holder of a microtome.

The microtome 90 is provided with limit switches 82, 86 and 88 (see FIG. 6) which are all connected to the electronic device 84. The limit switches 86 and 88 are not shown in FIG. 1 for clarity. The limit switch 82 detects when the vertically downward displacement of the guide mechanism 6 and the specimen clamping mechanism 12 reaches a lowermost position. The limit switches 86 and 88 detect when the sleeve 8 and the specimen clamping means 12 reach extremes of horizontal displacement.

The electronic device 84 is capable of generating two different output voltage levels, and pulses of three different lengths. One voltage level is 10 times higher than the other, and first, second and third pulse lengths are provided, the second pulse length being twice the first pulse length, and the third pulse length being three times the first pulse length. The voltage levels and the pulses of varying lengths can be fed to the electric motor 32 from the electronic device 84 by leads 48a and 48b.

Press-button control 62 serves to change the output voltage of the electronic device 84 from one level to another. One of the light emitting diodes 68 and 70 lights up depending upon which voltage level has been selected. The light emitting diode 68 lights up when the lower voltage level is selected, and the light emitting diode 70 lights up when the higher voltage level is selected.

Pressing the press-button controls 64 or 66 serves to cause the electronic device 84 to produce a continuous voltage level (which level is set by the switch 62), providing that the rotary switch 58 is in the correct position (see below). Pressing the press-button control 64 causes the motor 32 to be rotated in a direction which cuases displacement of the specimen clamping mechanism 12 along the axis 10 towards the cutting knife 110, and pressing the press-button control 64 causes the motor 32 to be rotated in the opposite direction so that the specimen clamping mechanism 12 is displaced along the axis 10 away from the cutting knife 110. This displacement is continuous so long as the control 64 or 66 is pressed, unless the displacement is sufficient to cause activation of limit switch 86 or 88. When either one of these switches is actuated the electronic device 84 stops further displacement in that direction. The switches 64 and 66 each incorporate light emitting diodes 112 and 114 respectively (see FIG. 6) which light up when movement is no longer possible in the direction controlled by that switch.

The rotary switch 58 is movable between four positions. In the "O" position, pressing of press-button control 64 or 66 will cause continuous movement of the specimen clamping mechanism 12 towards or away from the cutting knife 110 along the axis 10, providing that neither of the limit switches 86 or 88 has been actuated.

In the other three positions the press-button controls 64 and 66 cannot be operated, so that pressing either of these controls has no effect. In these three positions, the electronic device 84 generates a pulse which is fed to the motor 32, the pulse having three possible lengths depending upon the pulse length set by the rotary switch 58. The first pulse length corresponds to a movement of 5 μm, the second pulse lengths corresponds to a movement of 10 μm, and the third pulse length corresponds to a a movement of 15 μm. If the press-button control 62 has been pressed to set the high voltage level then the first second and third pulse lengths will correspond to a movement of 50 μm, 100 μm, and 150 μm respectively.

Figure 6:
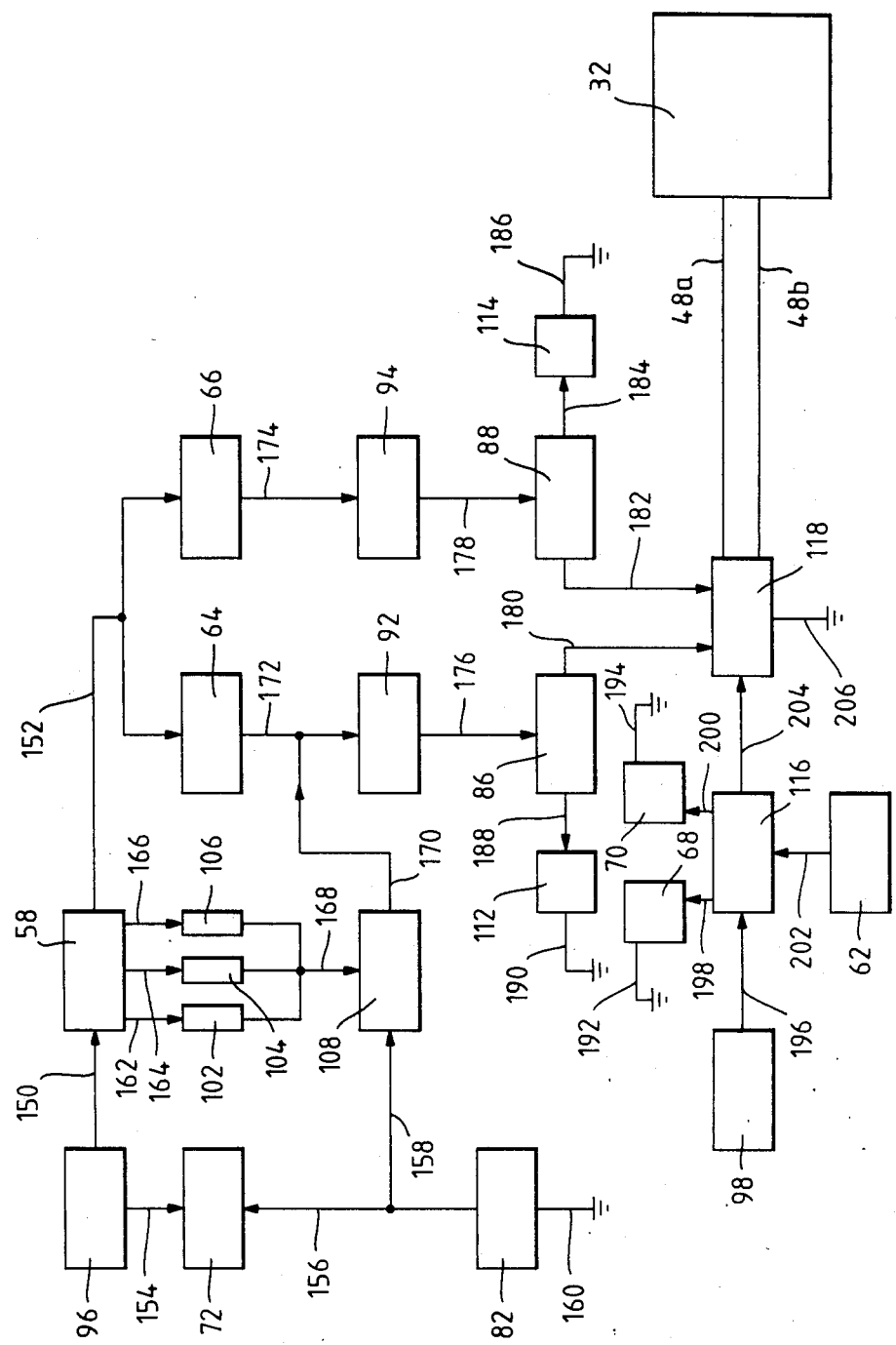
FIG. 6 is a schematic block diagram of an electronic device, a drive motor and controls for a microtome according to the invention.

FIG. 6 is a block diagram showing schematically the components of the electronic device 84 and the way it is connected to the other parts of the microtome 90.

Two stabilised D.C. voltage supplies 96 and 98 are provided; typically voltage supply 96 supplies 12 volts D.C. and voltage supply 98 supplies 22 volts D.C. The D.C. supplies 96 and 98 may be obtained in a standard manner by appropriate voltage reduction, rectification and smoothing of a mains A.C. supply.

The voltage supply 96 is connected by line 150 to the rotary switch 58. The rotary switch 58 has four output lines 162, 164, 166 and 152, and each output line corresponds to one of the four switch settings of the rotary switch 58. Output lines 162, 164 and 166 are connected to timing circuits 102, 104 and 106 respectively. The timing circuits 102, 104 and 106, when activated, are operative for time periods $T_1$, $T_2$ and $T_3$ respectively; $T_3$ is three times as long as $T_1$ and $T_2$ is twice as long as $T_1$. The outputs of the timing circuits 162, 164 and 166 are each connected to line 168, and line 168 is connected to a pulse generator 108.

The voltage supply 96 is connected to the cut counter 72 via line 154, and line 156 connects the cut counter 72 to the limit switch 82. The limit switch 82 is connected to earth via line 160. Line 156 is connected to a reset input of the pulse generator 108 via line 158.

The output line 152 of the rotary switch 58 is connected to both the press-button control 64 and to the press-button control 66. The press-button controls 64 and 66 are connected to a forward feed drive amplifier 92 and a return feed drive amplifier 94 respectively. Line 172 connects control 64 to the drive amplifier 92, while line 174 connects control 66 to the drive amplifier 94. An output of the pulse generator 108 is also connected to the forward feed amplifier 92 via a line 170 which is connected to the line 172.

The drive amplifier 92 is connected to the limit switch 86 by a line 176; the limit 86 serves to prevent the specimen clamping mechanism 12 being moved beyond the forwardmost position. The limit switch 86 is connected to the light emitting diode 112 by a line 188, and the light emitting diode 112 is connected to earth by a line 190. The limit switch 86 is connected to a switching device 118 by line 180. The limit switch 86 has first and second switch positions. In the first switch position a signal from the dirve amplifier 92 on the line 176 is transmitted via line 180 to the switching device 118, and no signal is transmitted on the line 188. In the second switch position of the limit switch 86 the signal from the drive amplifier 92 on the line 176 is transmitted along the line 188 to the light emitting diode 112, and along the line 190 to earth, causing the light emitting diode 112 to light. In the second switch position, no signal is transmitted on line 180.

The drive amplifier 94 is connected to the limit switch 88 by a line 178; limit switch 88 serves to prevent the specimen clamping mechanism 12 being moved beyond the rearmost position. The limit switch 88 is connected to a light emitting diode 114 by a line 184, and the light emitting diode 114 is connected to earth by a line 186. The limit switch 88 is connected to the switching device 118 by a line 182. The limit switch 88 has first and second switch positions. In the first switch position a signal from the drive amplifier 94 on the line 178 is transmitted via the line 182 to the switching device 118, and no signal is transmitted on the line 184. In the second switch position of the limit switch 88 the signal from the drive amplifier 94 on the line 178 is transmitted on the line 184 to the light emitting diode 114 and along the line 186 to earth, causing the light emitting diode 114 to light. In the second switch position, no signal is transmitted on the line 182.

The voltage supply 98 is connected to a voltage divider 116 by a line 196. The voltage divider 116 is operated by the press-button control 62 to which it is connected by a line 202. The voltage divider 116 is connected to the light emitting diode 68 by a line 198, and the light emitting diode 68 is connected to earth by a line 192. The voltage divider 116 is connected to the light emitting diode 70 by a line 200, the light emitting diode 70 being connected to earth by a line 194.

The output of the voltage divider 116 is connected to the switching device 118 by a line 204. The voltage divider 116, when actuated, serves to reduce the voltage output of the supply 98 transmitted from the line 196 to the line 204.

The press-button control 62 is movable between first and second positions. In the first position the voltage along the line 204 is reduced to a level which is sufficient to drive the motor 32 at a lower of the motor speeds, and a signal is transmitted along line 198 to light up the light emitting diode 68. In the second position of the press-button control 62 the voltage along the line 204 is sufficient to drive the motor 32 at the higher of the motor speeds, and a signal is transmitted along line 200 to light up light emitting diode 70.

The switching device 118 is connected to earth by a line 206, and has two outputs connected to leads 48a and 48b. The switching device 118 has first, second and third switch positions. In the first switch position line 204 is isolated and is not connected to either of leads 48a or 48b. The switching device 118 is in the first porition at all times, except when a drive signal is present on one of the lines 180 or 182.

In the second switch position of the switching device 118, the voltage on the line 204 is transmitted along lead 48a to the drive motor 32 in order to drive the motor 32 in one direction of rotation. The return signal from the motor 32 is transmitted along the lead 48b to earth by the line 206. The second switch position is actuated whenever a signal is transmitted to the switching device 118 on the line 180 from the drive amplifier 92.

In the third switch position of the switching device 118, the voltage on line 204 is transmitted along the lead 48b to the drive motor 32 in order to drive the motor 32 in the opposite direction of rotation. The return signal from the motor 32 is transmitted along lead 48a to earth via the line 206. The third switch position is actuated whenever a signal is transmitted to the switching device 118 on the line 182 from the drive amplifier 94.

The switching device 118 may be, for example, mechanical relays or may be a transistorised switching circuit.

The guide mechanism 6 together with the specimen clamping mechanism 12 are vertically displaceable relative to the cutting knife 92 between an uppermost position and a lowermost position. Typically the distance between the uppermost position and the lowermost position would be about 60 mm. In the uppermost position the specimen 18 in the specimen clamping mechanism 12 is above the cutting knife 110, and in the lowermost position the specimen 18 in the specimen clamping mechanism 12 is below the cutting knife 110.

The specimen clamping mechanism 12, together with the sleeve 8, is horizontally displaceable between a rearmost position and a forwardmost position, the specimen clamping mechanism 12 being closer to the cutting knife 110 in the forwardmost position than in the rearmost position.

In order to begin making cuts of the specimen 18 the specimen clamping mechanism 12 must first be displaced along the horizontal axis 10 to a position suitable for making a first cut. During this displacement, the specimen clamping mechanism 12 would typically be in the uppermost position.

The specimen clamping mechanism 12 can be brought to the position for making the first cut by setting rotary switch 58 to the "O" position and depressing press button control 64 which causes the electronic device 84 to trigger rough feed movement of the specimen clamping mechanism 12 along the axis 10 towards the cutting knife 110.

When the push button control 64 is pushed the electronic device 84 triggers the motor 32 which begins rotation of the drive shaft 44 about the axis 46 which is parallel to the axis 10. This causes rotation of the pinion 34 which drives the intermediate gearwheel 30. The intermediate gearwheel 30 drives the toothed ring 28. This rotates the micrometer nut 20 about the spindle 24 which is mounted in the guide mechanism 6 so as to be secured against axial movement. Consequently the rotation of the micrometer nut 20 results in a movement of the nut 20 together with the sleeve 8 and the specimen clamping mechanism 12 along the axis 10 towards the cutting knife 110.

The speed of movement towards the cutting knife 110 can be increased by a factor of ten by pressing the press button control 62, and can be reduced again by pressing the press button control 62 again. The press button control 64 is depressed long enough to bring the specimen clamping means to a position corresponding to the first cut.

If the press button control 64 is kept depressed then the movement along the axis 10 continues until the forwardmost position is reached when the limit switch 86 is actuated. This stops the electronic device 84 from outputting a voltage to the motor 32, thereby stopping the motor 32. At the same time the light emitting diode 112 provided on the press button control 64 lights up, and no further forward displacement is possible until the specimen clamping mechanism is displaced in the opposite direction, i.e. away from the cutting knife 110.

When the specimen clamping mechanism 12 is in the position for the first cut, the rotary switch 58 can be set to either the 5 μm, the 10 μm, or the 15 μm position or to the 50 μm, 100 μm, or 150 μm position. One of the lower three settings may be chosen for making rough first cuts when the specimen 18 is embedded in, for example, plastics while one of the higher three settings may be chosen for making rough first cuts when the specimen 18 is embedded in, for example, paraffin.

The vertical displacement of the specimen clamping mechanism 12 can then be activated, when the specimen clamping mechanism 12 moves to the lowermost position and the specimen 18 is cut by the cutting knife 110. When the specimen clamping mechanism reaches the lowermost position the limit switch 82 is actuated which causes a pulse having a length selected by the rotary switch 58 to be generated by the electronic device 84 and transmitted to the motor 32. This causes the specimen clamping mechanism 12 to be advanced by a rough cutting-thickness adjustment which is equal to the preselected distance set by the rotary switch 58.

Before the specimen clamping mechanism 12 moves back to the uppermost position it is temporarily retracted by a distance at least as great as the rough cutting-thickness adjustment to avoid contact with the cutting knife 110 during the upward movement. When the specimen clamping mechanism reaches the uppermost position the retraction is removed. The limit switch 82 also actuates the cut counter 72.

Further rough cuts can be made in this way. Each time the specimen clamping mechanism 12 reaches the lowermost position, the specimen clamping mechanism 12 is advanced by the set rough cutting-thickness adjustment towards the cutting knife 110 along the axis 10.

When a suitable surface has been formed on the specimen 18, switch 58 can be set to the "O" position and the precise thickness of the thin sections to be cut can be set using the setting knob 74 and the inspection window 76.

Rotation of the setting knob 74 causes rotation of the toothed wheel 300, and since the teeth of the toothed wheel 300 engage the teeth of the toothed wheel 306 the toothed wheel 306 also rotates. This causes rotation of the setting dial 307 which can be rotated until the desired cutting-thickness is set under the pointer 308.

The rotation of the setting dial 307 also rotates the shaft 310 and the cam device 312.

When the specimen clamping mechanism is in the uppermost position, the cam device 112 engages the lever of the mechanism 50 causing the lever and the mechanism 50 to rotate about the axis 10 for an angle depending upon the part of the cam device 312 which engages the lever.

It will be appreciated that the rotation of the mechanism 50 rotates the spindle 24 through a specific angle. As a result of this rotation micrometer nut 20, which does not rotate during the adjustment by the adjustment mechanism 50, is drive forward, i.e. towards the cutting knife 110, by a distance related to the angle of rotation of the spindle 24 and to the pitch of the spindle and the nut; this distance corresponds to the desired thickness of the thin section cuts to be made, and which is set on the setting dial 307.

The part of the cam device 312 which engages the lever can be altered by the setting knob 74 which rotates both the setting dial 307 and the cam device 312. The setting dial 307 is calibrated so that the reading set under the pointer 308 corresponds to the cutting-thickness adjustment caused by the mechanism 50.

When the lever moves out of engagement with the cam device 312 (as, for example, during the downward movement of the guide mechanism 6) the lever rotates back to its initial position without rotating the mechanism 50 or the spindle 24. When the lever moves back into engagement with the cam device 312 (as, for example, when the guide mechanism 6 moves back to the uppermost position) the lever and the mechanism 50 are once more rotated thereby advancing again the specimen clamping mechanism 12 by the desired thickness of the thin section cut.

When the thin section cuts have been made, the press button control 66 may be pressed to cause the return movement of the specimen clamping mechanism 12 towards the rearmost position. This return movement can continue until the limit switch 88 is actuated when further return movement is not possible and the light emitting diode 114 on the press button control 66 lights up. During the return movement of the specimen clamping mechanism 12 the electronic device 84 causes the motor to rotate in the opposite direction to the direction of rotation during the feed movement.

When the rough cuts are made, it is possible to obtain a maximum rough cutting-thickess by combining the rough cutting-thicknesses generated by the rotary switch 58, with a cutting-thickness set on the adjustment mechanism 50. It should be noted that during movement from the lowermost to the uppermost position, the specimen clamping mechanism 12 is retracted by an amount equal to the combined effect of the rough cutting-thickness adjustment and of the cutting-thickness set by the adjustment mechanism 50.

It should also be noted that the accuracy of the rough cutting-thicknesses set by the rotary switch 58 is as high as the accuracy of the cutting thicknesses set by the adjustment mechanism 50. Consequently if the thickness of the thin-section cuts to be made corresponds to one of the settings, then the rotary switch 58 can be used to set the distance to made the thin-section cuts, and the adjustment mechanism 50 can be set to a zero setting.

The operation of the electronic device 84 is as follows.

When the specimen clamping mechanism 12 is being brought to the position for the first cut the rotary switch is set in the "O" position which connects the line 150 with the line 152 so that the voltage from the voltage supply 96 is transmitted to the press-button controls 64 and 66. In this switch position of the rotary switch 58, the line 150 is not connected to any of the lines 162, 164 or 166.

When the press-button control 64 is pressed a signal on line 162 is transmitted on line 172 to the forward feed drive amplifier 92. If the press-button control 64 is released then this signal is no longer transmitted from the line 152 to the line 172.

The drive amplifier 92 amplifies the signal from the line 172 and transmits is along the line 176 to the limit switch 86. Provided that the limit switch 86 is in its first position, then the amplified signal is transmitted directly to the switching device 118 along line 180. This switches the switching device 118 to its second switch position and causes the voltage on line 204 to be transmitted on the lead 48a, as described above, and thereby energises the motor 32 to cause forward feed of the specimen clamping mechanism 12. This forward feed continues as long as the press-button control 64 is pressed, unless the specimen clamping mechanism 12 reaches the forwardmost position. If this happens then the limit switch 86 is switched from its first position to its second position. This prevents a signal from being transmitted on line 180, and at the same time causes a signal to be transmitted on line 188 to light up the light emitting diode 112. Since no signal is present on the line 180 the switching device 118 switches back to its first position and stops the motor 32.

When the specimen clamping mechanism 12 has reached the position for the first cut the rotary switch 58 is switched from the "O" position to one of its other three positions. The rotary switch 58 can be set so that the voltage supplied on the line 150 is connected to either line 162, line 164 or line 166. Selection of line 162 corresponds to a 5 μm or 50 μm rough cutting-thickness adjustment, selection of line 164 corresponds to a 10 μm or 100 μm rough cutting-thickness adjustment, and selection of line 166 corresponds to a 15 μm or 150 μm rough cutting-thickness adjustment.

Vertical movement of the specimen holder in the guide means 6 can then be actuated, for example, by a handwheel (not shown). The specimen holder 2 moves downwardly to the cutting knife 110 and a first rough cut of the specimen is made.

The downward movement continues until a lowermost position is reached, when the limit switch 82 is actuated causing a pulse to be fed along the line 156 to the cut counter 72 which increases the cut count on the cut counter 72 by one. A pulse is also fed on the line 158 to the reset input of the pulse generator 108. This resets the pulse generator 108 whereupon one of the timing circuits 102, 104 or 106 is activated (depending upon which selection has been made with the rotary switch 58) for a time $T_1$, $T_2$ or $T_3$ respectively. The timing circuits 102, 104 and 106 may, for example, be R.C. timing circuits which are reset by the pulse on the line 158.

The pulse generator 108 generates a pulse which has a duration proportional to $T_1$, $T_2$ or $T_3$. This pulse is transmitted on the line 170 to the line 172, and to the forward feed drive amplifier 92. This results in activation of the motor 32 for the duration of the pulse in the way described above, and causes the specimen clamping mechanism 12 to be moved forward by the amount of the rough cutting-thickness adjustment set on the rotary switch 58.

Operation of the microtome 90 continues in the way described above until all the required thin section cuts have been made, after which the return movement of the specimen clamping mechanism 12 can be effected by setting the rotary switch 58 to the "O" position, and by pressing the press-button control 66.

When the press-button control 66 is pressed the signal on the line 152 is transmitted on the line 174 to the return feed drive amplifier 94. If the press-button control 66 is released then the signal is no longer transmitted along the line 152 to the line 174.

The drive amplifier 94 amplifies the signal from line 174 and transmits it on the line 178 to the limit switch 88. Provided that the limit switch is in its first position, then the amplified signal is transmitted directly to the switching device 118 on the line 182. This switches the switching device 118 to its third position and causes the voltage on the line 204 to be transmitted on lead 48b as described above, and thereby energises the motor 32 to cause return movement of the specimen clamping mechanism 12. This return movement continues for as long as the press-button control 66 is pressed, unless the specimen clamping mechanism 12 reaches the rearmost position. If this happens then the limit switch 88 is switched from its first position to its second position. This prevents the signal from being transmitted on the line 182, and at the same time causes the signal to be transmitted on the line 184 to light up the light emitting diode 114. Since no signal is present on the line 182 the switching device 118 switches back to its first position and stops the motor 32.

We claim:

1. A microtome comprising
   a base
   a knife mounted on said base
   a guide means mounted for vertical motion on said base
   an elongated sleeve slidably mounted in said guide means, said sleeve being adapted to move along an axis extending horizontally and perpendicular to said knife, a specimen holder positioned at one end of said sleeve facing said knife, a bore extending into the distal end of said sleeve,
   a threaded spindle rotatably mounted on said guide means, one end of said spindle extending into said bore,
   first drive means for rotating said spindle,
   a nut adapted to threadably engage said spindle, said nut being rotatably mounted on said sleeve, and
   second drive means for rotating said nut, whereby, rapid feed or withdrawal of said sleeve is provided by rotation of the nut and fine feed of said sleeve is provided by rotation of said spindle.

2. The microtome according to claim 1 herein said first drive means is mounted on said guide means.

3. The microtome according to claim 2 wherein said first drive means is a mechanical feed mechanism.

4. The microtome according to claim 1 wherein a first gear extends radially from said nut and a second gear operatively connected to said second drive means engages said first gear.

5. The microtome according to claim 1 wherein said second drive means includes an electric motor.

6. The microtome according to claim 4 wherein said second drive means includes an electric motor and said second gear is an intermediate gear rotatably mounted on said sleeve.

* * * * *